United States Patent
Hamilton (10) Patent No.: US 7,131,950 B1
(45) Date of Patent: Nov. 7, 2006

(54) SYSTEM AND METHOD FOR NOISE REDUCTION IN THERMODILUTION FOR CARDIAC MEASUREMENT

(75) Inventor: Patrick S. Hamilton, Newton, MA (US)

(73) Assignee: E.P. Limited, Sommerville, MA (US)

( * ) Notice: Subject to any disclaimer, the term of this patent is extended or adjusted under 35 U.S.C. 154(b) by 561 days.

(21) Appl. No.: 10/252,758

(22) Filed: Sep. 23, 2002

(51) Int. Cl.
*A61B 5/02* (2006.01)
*A61B 5/08* (2006.01)

(52) U.S. Cl. .................. 600/504; 600/529; 600/484

(58) Field of Classification Search .............. 600/481, 600/488, 483–486, 504–508, 526
See application file for complete search history.

(56) References Cited

U.S. PATENT DOCUMENTS

| | | | | |
|---|---|---|---|---|
| 4,507,974 A | * | 4/1985 | Yelderman | 73/861.06 |
| 5,035,246 A | * | 7/1991 | Heuvelmans et al. | 600/486 |
| 5,146,414 A | * | 9/1992 | McKown et al. | 702/49 |
| 5,363,856 A | * | 11/1994 | Hughes et al. | 600/526 |
| 5,620,002 A | * | 4/1997 | Hughes | 600/526 |
| 5,687,733 A | * | 11/1997 | McKown | 600/505 |

* cited by examiner

*Primary Examiner*—Charles A Marmor, II
*Assistant Examiner*—Navin Natnithithadha
(74) *Attorney, Agent, or Firm*—Cesari and McKenna, LLP; Robert A. Cesari (57) ABSTRACT

A system and method for artifact reduction in thermodilution for cardiac measurement is provided by both respiration artifacts and noise artifacts are reduced. The system and method detects the beginning of a respiration cycle and estimates a respiration artifact which is subtracted from the thermosignal recorded.

20 Claims, 7 Drawing Sheets

SYSTEM AND METHOD FOR NOISE REDUCTION IN THERMODILUTION FOR CARDIAC MEASUREMENT

GOVERNMENT RIGHTS

This invention was made with government support under R44 HL54421 awarded by the National Heart, Lung, and Blood Institute of the National Institutes of Health (NIH). The Government has certain rights in the invention.

FIELD OF THE INVENTION

The present invention relates to the measurement of blood flow in cardiac output and, more specifically to the measurement of in vivo blood flow in cardiac output by thermodilution.

BACKGROUND OF THE INVENTION

Cardiac output, the average blood flow through the heart, is an important diagnostic measurement, especially for patients in coronary care units (CCU). Since the introduction of the Swan-Ganz catheter in the early 1970's, cardiac output has been routinely measured by thermodilution. The Swan-Ganz catheter is inserted into the femoral or subclavian vein and advanced so that a fluid port along the catheter is positioned in the right atrium (RA) and the tip of the catheter is in the pulmonary artery (PA). Generally, a 10 cc bolus of iced saline is injected through the fluid port along the catheter into the right atrium. A thermistor, or other temperature-sensing device, is located along the catheter within the pulmonary artery. The blood temperature is then monitored at the is thermistor as the blood flows through the pulmonary artery. The average cardiac output can be computed from the relative temperature fluctuation within the pulmonary artery. Specifically, the average cardiac output is an inverse function of the cooling as measured in the pulmonary artery.

There are two noted disadvantages to measuring cardiac output by bolus thermodilution. First, to avoid an undue fluid load on the patient, readings can only be taken periodically. Second, these periodic measurements are labor intensive as they require a nurse or other clinician to manually intervene to make each fluid injection.

Various methods proposed for the continuous method of cardiac output have typically involved substituting heat for chilled saline. U.S. Pat. No. 4,576,182, (the "'182 patent") titled METHOD AND APPARATUS FOR MEASURING LIQUID FLOW, issued to Richard A. Normann, describes an electrically resistive heating element wound around the outer surface of a catheter to introduce heat for thermodilution measurements. One advantage of such heating is that it can be electronically controlled, thereby allowing easier implementation of continuous monitoring systems. However, blood does not tolerate heating as well as it tolerates cooling. Consequently, the heating power that can be safely delivered to the blood is much less than the cooling power that is delivered by a 10 cc injection of iced saline. This lower heating power produces a much smaller heat pulse in the pulmonary artery. For example, an iced saline injection can produce a thermal fluctuation as large as 1–2° C., whereas the maximum thermal fluctuation that can be produced by heating, without damage to blood components, is between 10–20 m° C.

Figure 1:
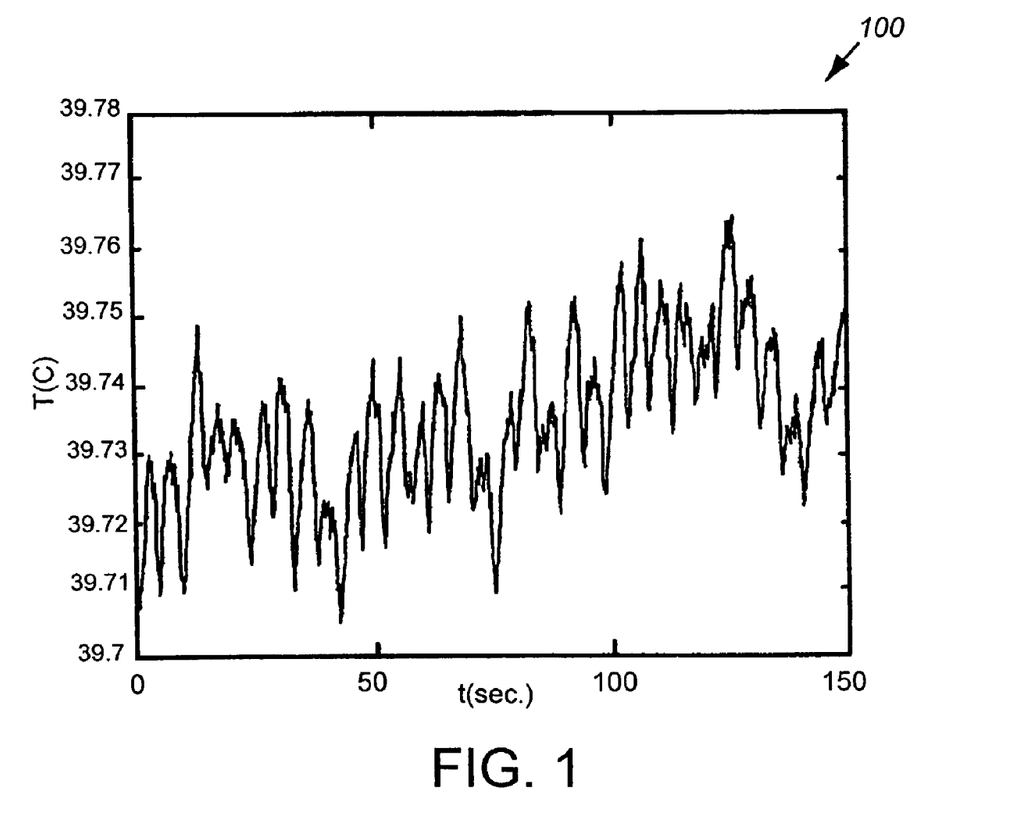
FIG. 1, already described, is a graph of a thermal signal sensed in the pulmonary artery of a pig attached to a respirator set at approximately 12 breaths per minute.

With such a small temperature fluctuation resulting from the heat pulses, thermal noise can make accurate thermal measurements of cardiac output difficult. FIG. 1 shows a thermal signal recorded in the pulmonary artery of a pig that was attached to a respirator set at a rate of approximately 12 breaths a minute. The approximate 20 m° C. regular fluctuations in FIG. 1 are the result of this respiration. The thermal noise generated by the respiration can significantly reduce the ability to detect a thermal pulse generated by a heating element on a catheter. Such noise in the thermal pulse recorded in the pulmonary artery can be reduced by averaging consecutive pulses. The accuracy of the thermal measurements increases with the number of pulses that are averaged, but as the number of pulses being averaged increases, the time required to generate an accurate estimate also increases to a length that reduces the usefulness of the procedure.

U.S. Pat. No. 4,507,974 (the '974 patent) titled METHOD AND APPARATUS FOR MEASURING FLOW, issued to Mark L. Yelderman, describes the application of a pseudo-random sequence of heat pulses to the measurement of cardiac output. The output of the downstream temperature sensor is cross-correlated with the pseudo-random sequence. The correlation materially reduces the effects of high-frequency thermal noise and a reasonable estimate of the thermal pulse signal can be obtained in five to eight minutes. However, low-frequency noise, primarily resulting from the effects of respiration is not reduced by this method.

U.S. Pat. No. 5,146,414 (the "'414 patent"), for a METHOD AND APPARATUS FOR CONTINUOUSLY MEASURING VOLUMETRIC FLOW, issued to Russell McKowan et al., describes a complex system for reducing low-frequency noise in thermal pulse measurements by matching the length of the pseudo-random sequence to a multiple of the respiration period. A reduction of the baseline artifact is obtained by estimating the artifact and subtracting it from the detected signal. This method works well when a patient is on a ventilator that imposes a uniform respiration rate. However, it is not easily applied to the irregular patterns that characterize normal respiration. Moreover, the baseline estimation described in the '414 patent is based on polynomial fitting to discrete points separated by 1–2 minutes, which provides only a rough estimate of very-low-frequency base line fluctuations and it thus introduces a significant delay before the thermal signal can be processed.

SUMMARY OF THE INVENTION

The present invention uses a pseudo-random sequence of heat pulses, with cross-correlation of the output of the downstream temperature sensor. This effectively removes high-frequency thermal noise. The low-frequency thermal noise resulting from the respiration artifact is reduced by subtracting an estimate of this noise feature from the thermal signal prior to correlation. More specifically, thermal artifact resulting from respiration is subtracted after detecting the respiration cycle by using a pressure sensor located in the inferior or superior vena cava. Other low frequency noise remaining after correlation is estimated from a moving average of the signal prior to correlation and subtracted after correlation. After noise reduction, the resulting signal may be used to more accurately estimate cardiac output.

Respiration cycles are detected using a cardiac output catheter which is modified to detect pressure fluctuations in the inferior vena cava or superior vena cava. An estimate of the typical thermal fluctuation produced by a respiration cycle is produced by averaging thermal data synchronized to the respiration cycles. The estimated fluctuations are then subtracted from the temperature signal whenever a respiration cycle is detected.

An estimate of the low-frequency noise that remains after correlation can be generated by analyzing the effect of the pseudo-random averaging on noise that is uncorrelated with the heating sequence. This estimate of the noise is then subtracted from the average pulse which thereby provides an improved estimate of the thermal pulse.

Cardiac output may then be estimated from the resulting thermal pulse estimate after the novel noise reduction process. The cardiac output may be calculated by any of a number of known methods including simple summation, curve fitting, or a combination of summation and curve fitting, applied to the thermal pulse estimate.

The foregoing system provides blood-flow measurements more quickly than prior arrangements that deal with respiratory and other low-frequency artifacts. At the same time, it provides materially higher accuracy.

BRIEF DESCRIPTION OF THE DRAWINGS

The above and further advantages of the invention may be better understood by referring to the following description in conjunction with the accompanying drawings in which like reference numerals indicate identically or functionally similar elements of which.

DETAILED DESCRIPTION OF AN ILLUSTRATIVE EMBODIMENT

Figure 2:
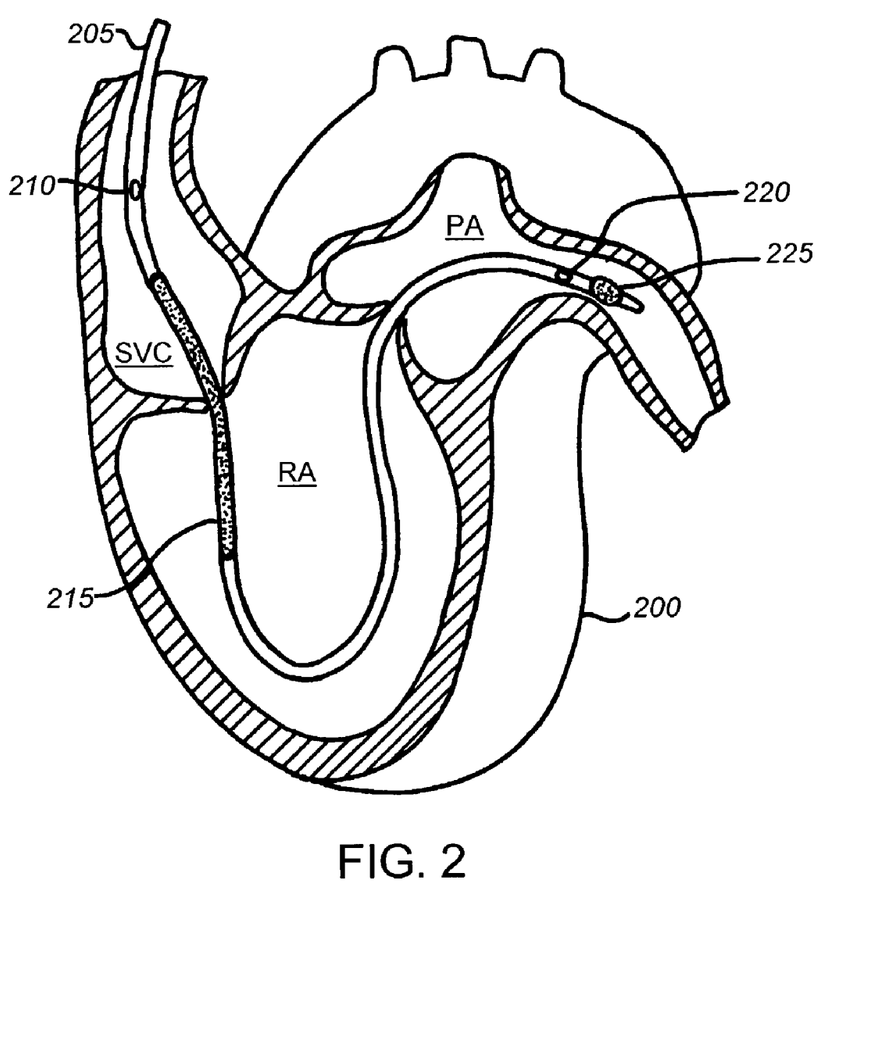
FIG. 2 is a cross section of a heart showing the position of a catheter having a heating element, a pressure port and a temperature sensing thermistor.

As shown in FIG. 2, a catheter 205 includes a pressure port 210 that allows the catheter system to monitor the pressure in the superior vena cava (SVC) or the inferior vena cava (IVC) (not shown). Typical respiration produces pressure fluctuations on the order of 3–7 mmHg in the IVC and the SVC. In the illustrative embodiment, respiration cycles are detected from these fluctuations. The catheter 205 also includes an electrical heat source 215 that generates sequences of heat pulses as described herein. A thermistor 220 senses the temperature of the blood in the pulmonary artery. Additionally, the catheter 205 includes a balloon 225 that allows the catheter to be flow-directed through the circulatory system of a patient.

Figure 3:
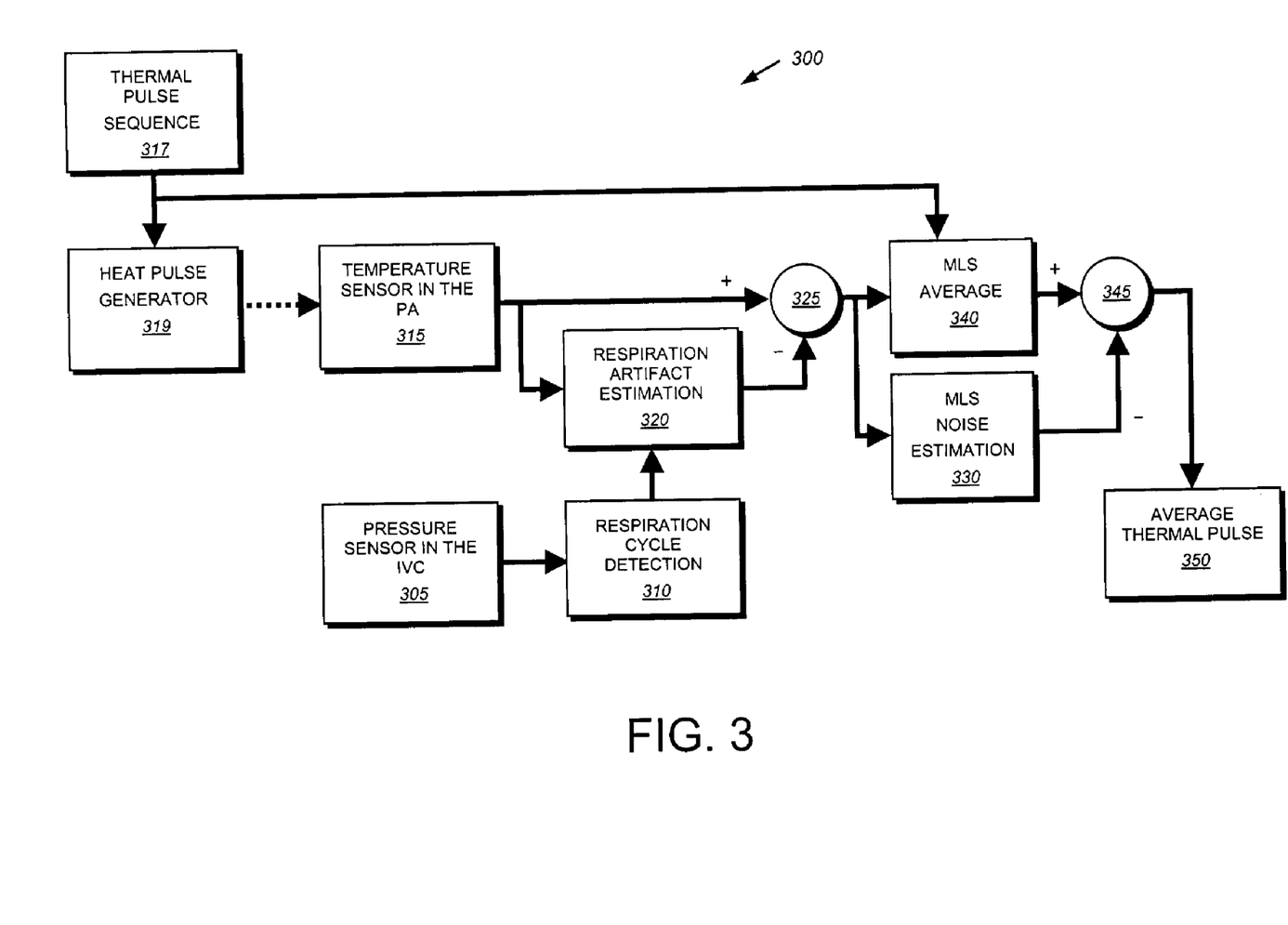
FIG. 3 is a flow chart detailing the procedure performed to reduce artifacts in the thermal signal.

FIG. 3 is a diagram of the steps of a procedure 300 in accordance with an illustrative embodiment of the present invention. In step 305, the inferior vena cava pressure is sampled and digitized. In the illustrative embodiment, this sampling of the pressure fluctuations from respirations occurs at a rate of 10 Hz; however higher or lower sampling rate may be utilized. The pressure sample is fed to a respiration cycle detector (step 310). The respiration cycle detection provides an input to step 320 which estimates blood flow artifacts due to respiration. In alternate embodiments, the detection of a respiration may be accomplished by various methods. One example of a method for detecting a respiration cycle would use nasal air flow. Another would use chest contractions and/or expansions of the subject.

Simultaneously, the thermal signal from the pulmonary artery is obtained in step 315 from the thermistor 220. The thermal signal is preferably sampled at the same rate that IVC pressure is sampled. The thermal signal is generated by a thermal pulse sequence (step 317) being fed into a heat pulse generator (step 319). In the illustrative embodiment the heat pulse generator is an electrical heat source 215 on a catheter 205. The thermal pulse sequence generated in step 317 is also fed into step 340, described further below. The thermal signal is applied to step 320, to estimate the respiration artifact in that signal. Additionally, the signal is fed to an adder, where the estimated respiration artifact is subtracted from the thermal signal in step 325.

Figure 4:
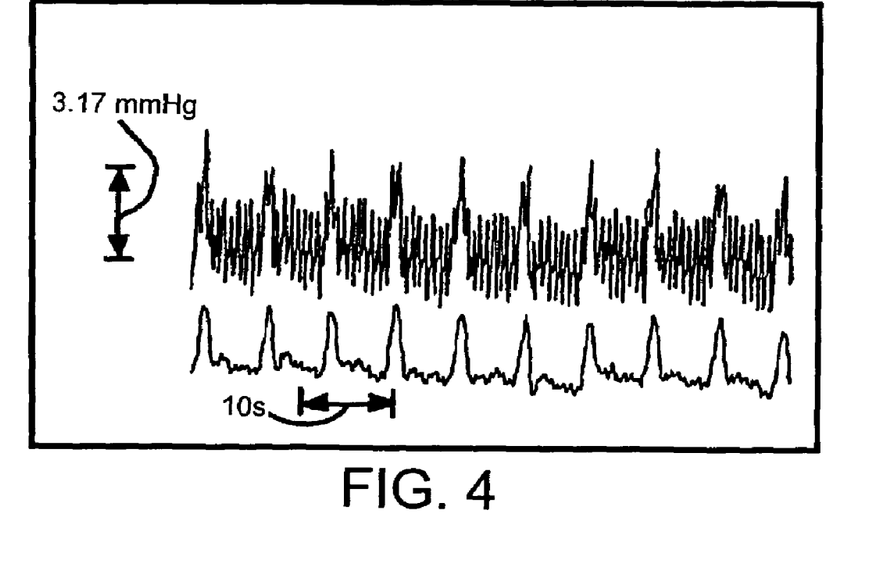
FIG. 4 is a trace of a pressure signal recorded from the inferior vena cava of a pig.

A typical pressure signal recorded from inferior vena cava of an anesthetized pig on a ventilator is shown on the upper trace of FIG. 4. The rapid fluctuation of the signal is the result of the cardiac rhythm, while the slower fluctuations are the result of respiration. In an illustrative embodiment of the invention, the cardiac fluctuations are removed by a moving average filter. Assuming a 10 Hz sample rate, an eight-sample filter is preferred as it produces a null at 1.25 Hz, which effectively eliminates fluctuations resulting from heart rates of approximately 75 beats per minute (bpm). One skilled in the art will realize that other types of filters may also be used to reduce the cardiac fluctuations, including, but not limited to, iterative filters, cascades of moving average filters and adaptive filters if an ECG signal is used to obtain an accurate, independent detection of cardiac cycles.

The lower trace of FIG. 4 represents the pressure signal after it has been filtered to reduce the cardiac-induced fluctuations. Illustratively, a respiration cycle is detected when the filtered pressure signal exceeds 75% of the maximum signal value over the previous six seconds. Each time a respiration cycle is detected in step (310), the present estimate of the thermal artifact produced by respiration is aligned with, and subtracted from, the thermal signal. A portion of the original signal that corresponds to the present estimate is then used to generate a new artifact estimate.

Figure 5:
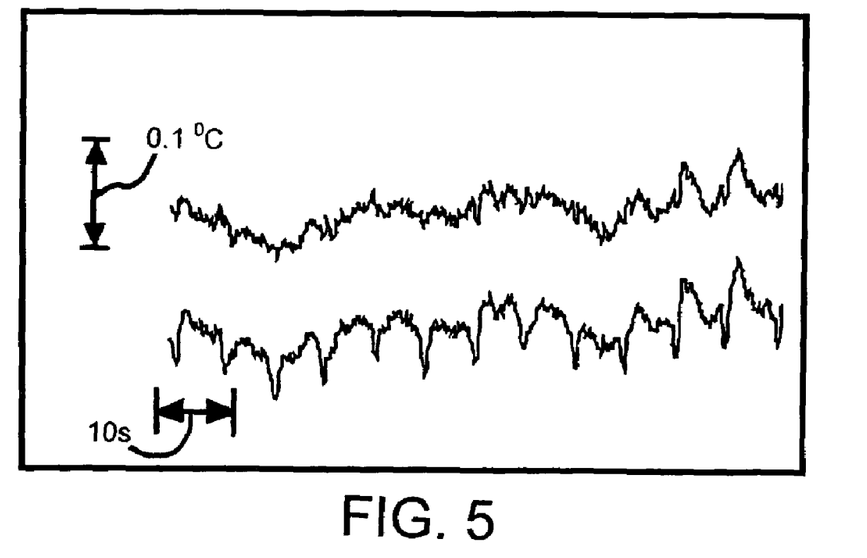
FIG. 5 is a pressure signal showing periodic respiration artifacts.

A typical thermal recording exhibiting periodic respiration artifacts is shown in the lower trace of FIG. 5. Subtraction of respiration thermal artifacts results in the upper trace of FIG. 5.

Figure 6:
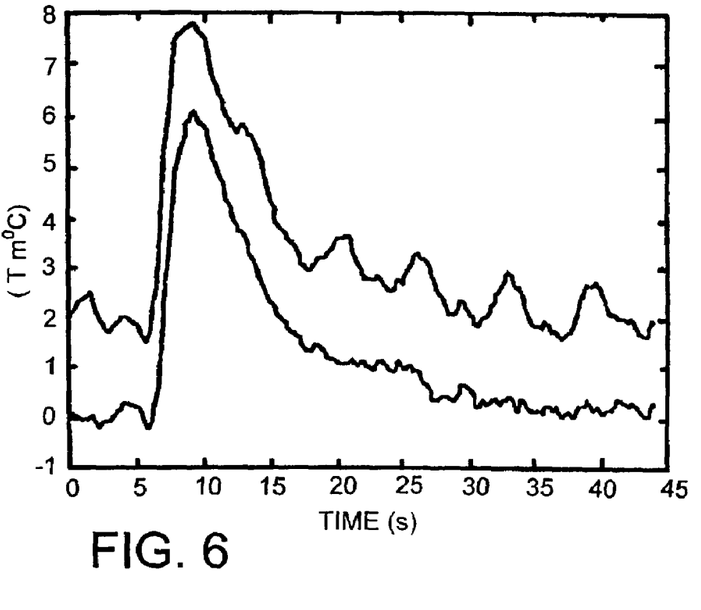
FIG. 6 is a signal recording showing the effect of removing respiration artifacts on an average thermal pulse.

FIG. 6 illustrates the effect of removing respiration artifacts from such an averaged thermal pulse. The upper trace of FIG. 6 represents an averaged thermal pulse produced without removal of respiration artifacts, while the lower trace of FIG. 6 represents the same averaged thermal pulse produced when respiration artifacts are removed by the present invention.

Following the removal of the respiration artifact, the average thermal pulse arriving in the pulmonary artery as a result of thermal pulses generated in the right atrium is estimated using MLS averaging.

The pseudo-random pulse sequence generated by 317 is a binary Maximum Length Sequence, or a sequence of 0s and 1s derived from a Maximum Length Sequence. A binary MLS sequence consists of N binary digits where:

$$N = 2^n - 1$$

and where $$\frac{(N+1)}{2}$$

of the digits are 1s and $$\frac{(N-1)}{2}$$

of the digits are 0s. Each digit of the sequence represents the control input for the heat pulse generator over a heat pulse interval.

The output of the subtraction process of step 325 is fed into steps 330 and 340. The pseudo-random pulse sequence generated by step 317 to control the heat source are also input into step 340. Step 340 generates a Maximum Length Sequence (MLS) average. Step 330 generates an estimate of the noise in the MLS average, and step 345 subtracts the MLS average noise estimate from the MLS average. The result of the subtraction is the average thermal pulse (step 350).

It is well known to those skilled in the art that when repetitive pulses are corrupted by uncorrelated noise, averaging a number of successive pulses produces an average pulse with greatly reduced noise. Because the thermal noise in the pulmonary artery is uncorrelated with the thermal pulses produced for thermodilution, successive thermal pulses detected in the pulmonary artery will thus produce an average pulse where the additive noise is reduced. However, a thermal pulse may last as long as 30 seconds, and it can take a significant amount of time to average enough thermal pulses to achieve an acceptable signal-to-noise ratio in the average pulse.

The time required for generating a suitable average thermal pulse from a collection of noisy pulses can be reduced by allowing the thermal pulses to overlap. If the sequence of thermal pulses is produced with a maximum length sequence (MLS) of length 2N−1 (N pulses and N−1 periods without a pulse), as taught by the '974 patent, averaging N overlapping pulses produces an average pulse with an added DC component proportional to the area of the original pulse. More information on the properties of MLS sequences can, for example, be found in Ziemer, R. E., and R. L. Peterson, *Digital Communications and Spread Spectrum Systems*, Macmillan Publishing Company, New York, 1985, which is hereby incorporated by reference.

Noise in the MLS average is most effectively reduced for noise periods that are substantially shorter than the period of the MLS sequence. Noise is not as effectively reduced when the period of the noise approaches or is longer than the MLS sequence. By examining how the MLS averaging process affects the noise in the resulting average, we can show that there is a simple method for estimating the noise signal in the MLS average from the original signal. With this noise estimate subtracted from the MLS average, the low frequency noise in the MLS average is materially reduced.

More specifically, we generate an average thermal pulse in the pulmonary artery by adding N overlapping intervals of thermal data where each interval is synchronized with a heat pulse, and N is the number of pulses in the MLS. We can represent this MLS average as follows:

$$\tilde{p}_0[i] = \sum_{t=t_0}^{t_0 - 2N + 2} rnd[t] \cdot x[t+i] \tag{1}$$

Where $\tilde{p}_0[i]$ is the ith sample of our MLS average, $rnd[t]$ represents our MLS sequence at time t, $x[t+i]$ is a sample from the thermal data at time t+i, and 2N−1 is the length of the MLS sequence.

For any $x[t_n+i]$, where $t_n$ represents the time a heat pulse is triggered, the actual sample value can be broken down into the portion of the value caused by a heat pulse initiated at $t_n$, the portion of the signal resulting from pulses triggered before and after $t_n$, and the value of the noise signal at $t_n+i$. Thus $x[t_n+i]$ can be written as:

$$x[t_n + i] = n[t_n + i] + p[i] + \sum_{j \neq 0} rnd(t_n - j) \cdot p[t_n - j + i] \tag{2}$$

where p[i] is the ith sample of a thermal pulse and n[t] is additive noise.

Noting that the expected value of $rnd[i] \cdot p[i]$ is $p[i]/2$ and taking the expected value of (2) gives:

$$E\{x[t_n + i]\} = \frac{p[i] + P}{2} + n[t_n + i] \tag{3}$$

where P is the area of the thermal pulse.

Substituting (3), the expected value for x[t+i], for x[t+i] in (1), taking the expected value of (1), and noting that we sum N data sequences where rnd[t]=1, gives:

$$E\{\tilde{p}_0[i]\} = N \cdot \left[\frac{p[i] + P}{2}\right] + \frac{1}{2} \sum_{j=0}^{2N-2} n[t_0 - j + i] \tag{4}$$

From (4) we see that the signal produced by averaging overlapping thermal pulses consists of three components: the thermal pulse signal, a DC component equal to N/2 times the area of the thermal pulse, and a filtered noise signal. The MLS averaging process effectively low-pass filters the noise with a moving average filter. The length of the averaging window is equal to the length of the MLS sequence, and the magnitude of the frequency response is:

$$|H(f)| = \left|\frac{\sin((2N-1) \cdot Tf\pi)}{(2N-1) \cdot Tf\pi}\right| \tag{5}$$

where T is the duration of each heat pulse. Choosing the duration of the pseudo-random sequence is a tradeoff between lag in the estimate of cardiac output and reduction in low frequency noise.

From (4) it is apparent that the noise in the MLS average can be estimated by averaging the original signal over a window equal to the length of the pseudo-random sequence. This window-averaged noise estimate can be written as:

$$\hat{n}_0[i] = \sum_{t=t_0}^{t_0-2N+2} x[t+i] \quad (6)$$

where, similar to (2):

$$x[t+i] = n[t+i] + \sum_j rnd[t+i+j] \cdot p[j] \quad (7)$$

Equation (7) differs slightly from (2) because (7) makes no assumptions that t is synchronized with a heat pulse (rnd[t] =1). We can then express the expected value of (7) as:

$$E\{x[t+i]\} = n[t+i] + \frac{P}{2} \quad (8)$$

Substituting (8) into (6) to give the expected value of (6):

$$E\{\hat{n}_0[i]\} = \sum_{j=0}^{2N-2} n[t_0 - j + i] + \frac{(2N-1) \cdot P}{2} \quad (9)$$

Dividing (9) by two and subtracting it from (4) yields an improved thermal pulse estimate with an expected value of:

$$E\left\{\tilde{p}_0[i] - \frac{1}{2}\hat{n}_0[i]\right\} = \frac{N \cdot p[i]}{2} + \frac{P}{4} \quad (10)$$

After subtracting half the window-averaged signal, the noise term drops out of expected value, leaving only the thermal pulse term and a DC offset proportional to P.

Figure 7:
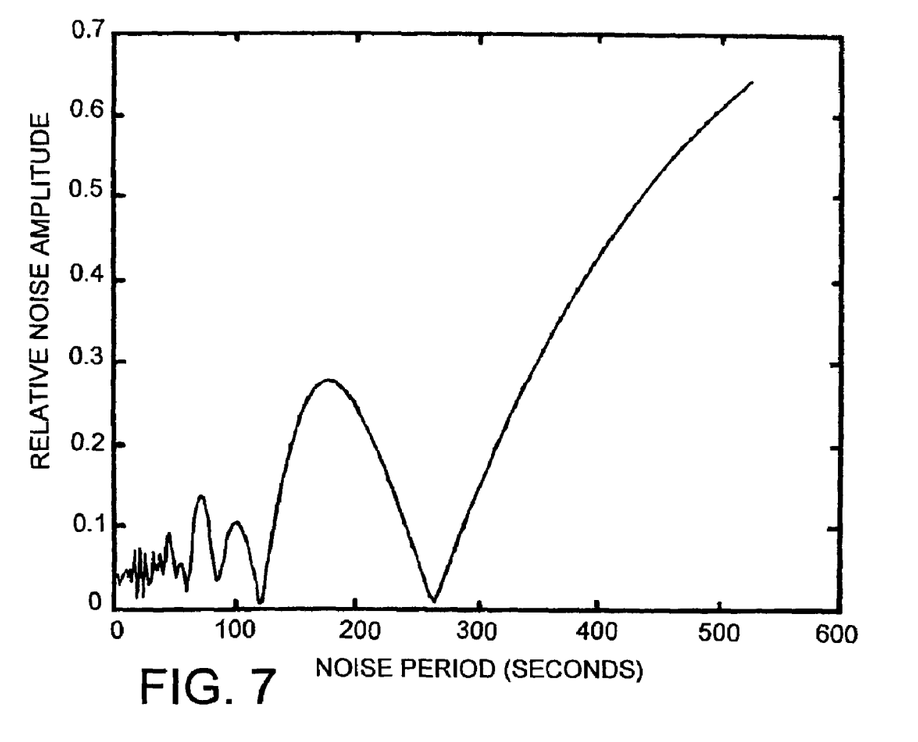
FIG. 7 is a diagram showing the relative noise amplitude when using a MLS average in accordance with an embodiment of the present invention.
Figure 8:
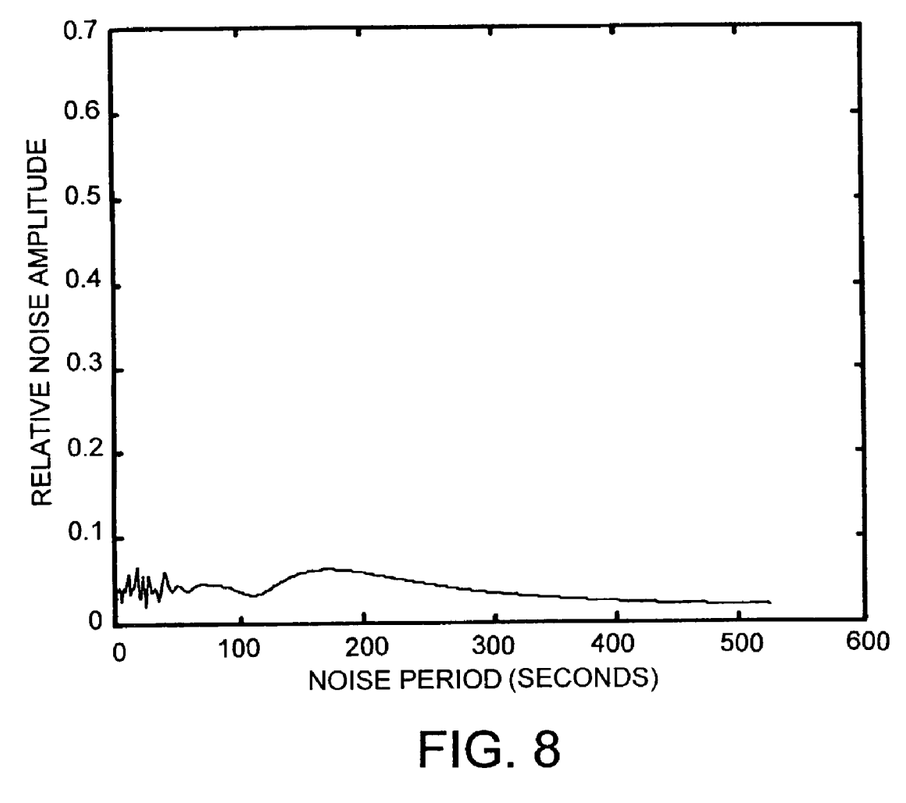
FIG. 8 is a diagram showing the relative noise amplitude in a thermal signal when utilizing MLS average and MLS noise reduction in accordance with an embodiment of the present invention.

Though (10) implies that all noise can be removed from the estimate of p[i], it is only an approximation of the real case. In the illustrative embodiment, the MLS sequence lasts 255.5 seconds and contains 256 half-second heat pulses. We used MATLAB to simulate the actual filtering performed by (4) and (10) with an MLS sequence with a length of 255.5 seconds. FIG. 7 is a plot of the relative noise amplitude of (4) for a range of noise periods. FIG. 8 is a plot of the relative noise amplitude of (10) over the same range of noise periods. Equation (10) offers no significant improvement over 4 for noise with periods that are shorter than one-third the length of the MLS sequence; however, it offers a clear reduction for noise having periods longer than approximately one-third the MLS sequence length.

Figure 9:
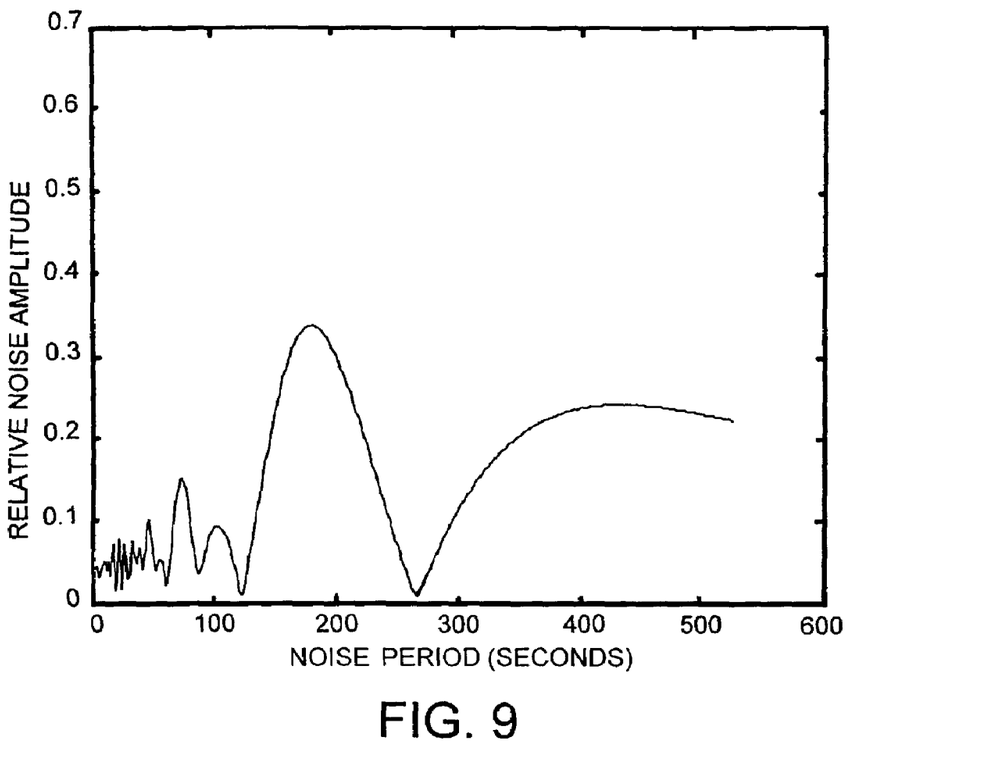
FIG. 9 is a diagram showing the relative noise amplitude in a thermal signal when using a baseline filter and MLS averaging.

Other methods have been proposed for removal of thermal drift, with the most straight forward being window averaging the temperature signal to obtain an estimate of the baseline drift and subtracting this estimate from the temperature signal before MLS averaging. This is equivalent to the method proposed by the '414 patent, where the baseline noise is estimated by extrapolating between points generated by averaging over a window equal to that of the MLS sequence length. FIG. 9 is a plot of the relative noise transmission when low frequency noise is estimated with a moving window average and subtracted prior to MLS averaging. This approach actually increases noise, relative to MLS averaging alone, for noise with periods close to half the MLS sequence length. Although it reduces noise, relative to MLS averaging alone, for noise periods greater than the length of the MLS averaging sequence, the reduction is much less than that resulting from (10). Additionally, point-by-point subtraction of a moving-window average requires that the signal be delayed by half the averaging window width before the noise estimate is subtracted, adding significantly to the lag in the estimate of cardiac output.

To again summarize, a pseudo-random series of thermal pulses is originated in the right atrium. An estimate of the thermal fluctuation produced by a respiration cycle is generated by averaging thermal data synchronized to respiration cycles, which are detected by a pressure port in the superior or inferior vena cava. The estimated thermal fluctuations from respiration are subtracted from the thermal signal received in the pulmonary artery. The resulting signal is then processed to provide a maximum length sequence (MLS) average estimate and an estimate of the noise in the MLS average. Again, the noise estimate is subtracted from the MLS average to produce an improved estimate of the thermal pulse generated by a heat pulse. The resulting thermal pulse estimate can then be used to calculate the average cardiac output using known methodologies.

The system and method described for reducing noise in thermal dilution techniques for cardiac output measurement utilizes a noise estimate to be subtracted from the MLS average produced. Unlike the method described in the '974 patent, the present invention utilizes both the removal of an estimated respiration artifact and an estimated noise value to improve the average thermal pulse estimate. The pseudo-random thermal pulse sequence is not required to be a multiple of the respiration period, as respiration cycles are detected from pressure fluctuations in the inferior or superior vena cava. Thus, the present invention is operable when the patient is not on a respirator or otherwise engaged in a constant or consistent respiration pattern.

The foregoing has been a detailed description of illustrative embodiments of the invention. Various modifications and additions can be made without departing from the spirit and scope of the invention. While this description has been written in terms of using sampled pressure in the inferior vena cava for the detection of respiration, it is expressly contemplated that sampled pressure in the superior vena cava can also be used. It is expressly contemplated that any of the operations and procedures described herein can be implemented using hardware, software comprising a computer-readable medium having program instructions executing on a computer or a combination of hardware and/or software. Accordingly this description is to be taken only by way of example and not to otherwise limit the scope of the invention.

What is claimed is:

1. A method for measuring average flow using thermodilution, the method comprising the steps of:
   generating a pseudo-random heat pulse sequence;
   measuring a thermal signal downstream of the generated psuedo-random heat pulse sequence;

generating a maximum length sequence noise estimate and a maximum length sequence average;

subtracting the maximum length sequence noise estimate from the maximum length sequence average to generate an average thermal pulse; and estimating the average flow from the average thermal pulse.

2. The method of claim 1 wherein the flow measured is cardiac output.

3. The method of claim 1 wherein the maximum length sequence noise estimate is calculated by summing the thermal signal over a moving window equal in length to the maximum length sequence.

4. A method for measuring average flow using thermodilution, the method comprising the steps of:

generating a pseudo-random heat pulse sequence;

measuring a thermal signal downstream of the generated heat pulse sequence;

subtracting an estimated periodic noise artifact from the measured thermal signal;

generating a maximum length sequence noise estimate and a maximum length sequence average;

subtracting the maximum length sequence noise estimate from the maximum length sequence average to generate an average thermal pulse; and estimating the average flow from the average thermal pulse.

5. The method of claim 4 wherein the estimated periodic noise artifact results from respiration.

6. The method of claim 4 wherein the step of subtracting the respiration artifact further comprising the steps of:

detecting a respiration cycle;

aligning and subtract an estimated average artifact from the thermal signal;

updating the estimated average artifact by averaging successive artifacts aligned by the respiration cycle detection.

7. The method of claim 6 wherein a respiration cycle is detected from pressure fluctuations in a vein.

8. The method of claim 7 wherein the vein is selected from a group consisting of a superior vena cava and an inferior vena cava.

9. The method of claim 7 wherein the step of detecting a respiration cycle further comprises the steps of:

detecting pressure fluctuations in a vein to generate a pressure fluctuation signal;

filtering the pressure fluctuation signal to reduce cardiac related pressure fluctuations; and detecting when the pressure fluctuation signal crosses a threshold based on previous signal maxima.

10. The method of claim 6 wherein the reference point of a respiration cycle is detected from monitoring nasal air flow.

11. The method of claim 6 wherein a respiration cycle is detected from monitoring chest expansion and contraction.

12. The method of claim 6 wherein a respiration cycle is determined from the output of a ventilator.

13. The method of claim 4 wherein the maximum length noise sequence estimate is calculated by summing the thermal signal over a moving window the equal in length to the maximum length sequence.

14. A method for measuring average flow using thermodilution, the method comprising the steps of:

generating a heat pulse sequence;

measuring a thermal signal down steam from the generated heal pulse sequence;

subtracting an estimated periodic artifact from the measured thermal signal to generate a resulting thermal signal;

estimating the average flow from the resulting thermal signal;

wherein the step of subtracting the estimated periodic artifact comprises the steps of:

detecting a respiration cycle, aligning and subtracting an estimated average artifact from the measured thermal signal and updating the estimated average artifact by averaging successive artifacts aligned by the respiration cycle detection.

15. The method of claim 14 wherein the respiration cycle is detected from pressure fluctuations in a vein.

16. The method of claim 15 wherein the vein is selected from a group consisting of a superior vena cava and an inferior vena cava.

17. The method of claim 14 wherein the step detecting the respiration cycle further comprising the steps of:

detecting pressure fluctuations in a vein to generate a pressure fluctuation signal;

filtering the pressure fluctuation signal to reduce cardiac related pressure fluctuations; and detecting when the pressure fluctuation signal crosses a threshold based on a previous signal maxima.

18. The method of claim 14 wherein the respiration cycle is detected by monitoring nasal air flow.

19. The method of claim 14 wherein the respiration cycle is detected from monitoring chest expansion and contraction.

20. The method of claim 14 wherein the respiration cycle is determined from the output of a ventilator.

* * * * *